US00PP08646P

United States Patent [19]

Zary

[11] Patent Number: Plant 8,646

[45] Date of Patent: Mar. 22, 1994

[54] HYBRID TEA ROSE PLANT NAMED 'JACPOW'

[75] Inventor: Keith W. Zary, Thousand Oaks, Calif.

[73] Assignee: Bear Creek Gardens, Inc., Medford, Oreg.

[21] Appl. No.: 991,089

[22] Filed: Dec. 15, 1992

[51] Int. Cl.[5] ..... A01H 5/00

[52] U.S. Cl. ..... Plt./11

[58] Field of Search ..... Plt. 18, 11, 14

[56] References Cited

U.S. PATENT DOCUMENTS

Plt 5067 7/1983 Meilland ..... Plt/11

Plt 5575 10/1985 Kordes, et al. ..... Plt/18

*Primary Examiner*—Howard J. Locker

*Attorney, Agent, or Firm*—Klarquist, Sparkman, Campbell, Leigh and Whinston

[57] ABSTRACT

A hybrid tea class rose plant having a vigorous, upright growth; good production as a greenhouse cut flower; long, straight stems; attractive white-with-delicate-pink-blush flower and quick cycle time.

1 Drawing Sheet

The present invention relates to a new and distinct variety of rose plant of the Hybrid Tea class which was originated by me by crossing the variety JAChop, U.S. Plant Pat. No. 6,653, with the variety KORflug, U.S. Plant Pat. No. 5,575.

The primary objective of this breeding was to produce a new rose variety having the high production and fast cycle time of JAChop combined with the light pink color and flower size of KORflug. The objective was substantially achieved along with other desirable improvements as evidenced by the following unique combination of characteristics which are outstanding in the new variety and which distinguish it from its parents, as well as from all other varieties of which I am aware:

1. Good production (200 stems per $m^2$) for a large-flowered greenhouse cut flower rose;
2. Quick cycle time for a large-flowered rose;
3. An attractive white rose with a delicate pink blush;
4. Long, straight stems;
5. Vigorous, upright growth.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—JAChop, U.S. Plant Pat. No. 6,653.

*Pollen parent.*—KORflug, U.S. Plant Pat. No. 5,575.

Classification:

*Botanical.*—Rosa hybrida.

*Commercial.*—Hybrid Tea.

FLOWER

Observations made from specimens grown in a greenhouse environment in Somis, Calif., from Jan. through Jun., 1992.

Blooming habit: Recurrent. Cycle time is generally one week faster than other hybrid tea cut roses of the color range.

Bud:

*Size.*—1¾" when the petals start to unfurl.

*Form.*—Long, pointed, ovoid.

*Color.*—When sepals first divide, bud color is Yellow White Group 158D with a distinct line of Red Group 46D on the petal edges. When half blown, the upper and lower sides of the petals are White Group 155B with petal edges being Red Group 49B. The Red Group 49B gradually spreads across the petals as the flower opens.

*Sepals.*—Color: Green Group 138B. Surface texture: Covered with fine hairs. There are three normally appendaged sepals. There are two unappendaged sepals with hairy edges.

*Receptacle.*—Color: Green Group 137C. Shape: Apple. Size: Large, 7/16"×7/16". Surface: Smooth.

*Peduncle.*—Length: Long, 4". Surface: Smooth with occasional glands. Color: Medium green. Strength: Stiff, erect.

Bloom:

*Size.*—Large. Average open size is 5".

*Borne.*—Singly.

*Stems.*—Long, strong, 24" to 28".

*Form.*—When first open: High centered. Permanence: Outer petals curl back.

*Petalage.*—Number of petals under normal conditions: 35.

*Color.*—The upper and reverse sides of the petals are White Group 155B with Red Group 49B on the petal edges. The Red Group 49B gradually spreads across the petals as the flower opens. The bases of the petals have a small (⅛×⅛"), greenish white half moon at the point of attachment. The major color on the upper side is White Group 155B.

*Variegations.*—None.

*Discoloration.*—No change in general tonality at the end of the first day. By the end of the third day: A gradual spreading of Red Group 49B over the petal surface occurs.

*Fragrance.*—Slight.

Petals:

*Texture.*—Thick.

*Shape.*—Round.
*Form.*—Tips slightly recurved.
*Arrangement.*—Imbricated, with few petaloids in the center.
*Persistence.*—Drop off cleanly.
*Lastingness.*—On the plant: Long, 5 to 6 days. As a cut flower: Long, 7 to 8 days.

Reproductive parts:
*Anthers.*—Size: Medium. Quantity: Many. Color: Yellow. Arrangement: Regular around the styles.
*Filaments.*—Color: White.
*Pollen.*—Color: Lemon yellow.
*Styles.*—Color: Yellow.
*Stigmas.*—Color: Greenish white.

Form: Bush.

Growth: Vigorous, upright and branching.

Foliage: Number of leaflets on normal mid-stem leaves: 5.
*Size.*—Large, 6″×4″.
*Quantity.*—Normal.
*Color.*—New foliage: Light green. Old foliage: Dark green.

Leaflets:
*Shape.*—Pointed oval.
*Texture.*—Upper side: Smooth.
*Edge.*—Serrated.
*Serration.*—Single, small.

*Petiole rachis.*—Color: Green with some reddish cast.
*Petiole underside.*—Smooth with occasional prickles.
*Stipules.*—Short, bearded and edged with glands.
*Disease resistance.*—Susceptible to mildew under normal growing conditions in a greenhouse environment at Somis, Calif.

Wood:
*New wood.*—Color: Light green. Bark: Smooth.
*Old wood.*—Color: Green. Bark: Smooth.

Prickles:
*Quantity.*—On main canes from base: Ordinary. On laterals from main canes: Ordinary.
*Form.*—Medium, hooked downward.
*Color when young.*—Red.

Small prickles:
*Quantity.*—On main stalks: None. On laterals: None.

I claim:

1. A new and distinct variety of rose plant of the hybrid tea class, substantially as herein shown and described, characterized particularly as to novelty by the unique combination of its vigorous upright growth, its good production as a greenhouse cut flower, its long straight stems, and its attractive white-with-delicate-pink-blush flower and quick cycle time.

* * * * *

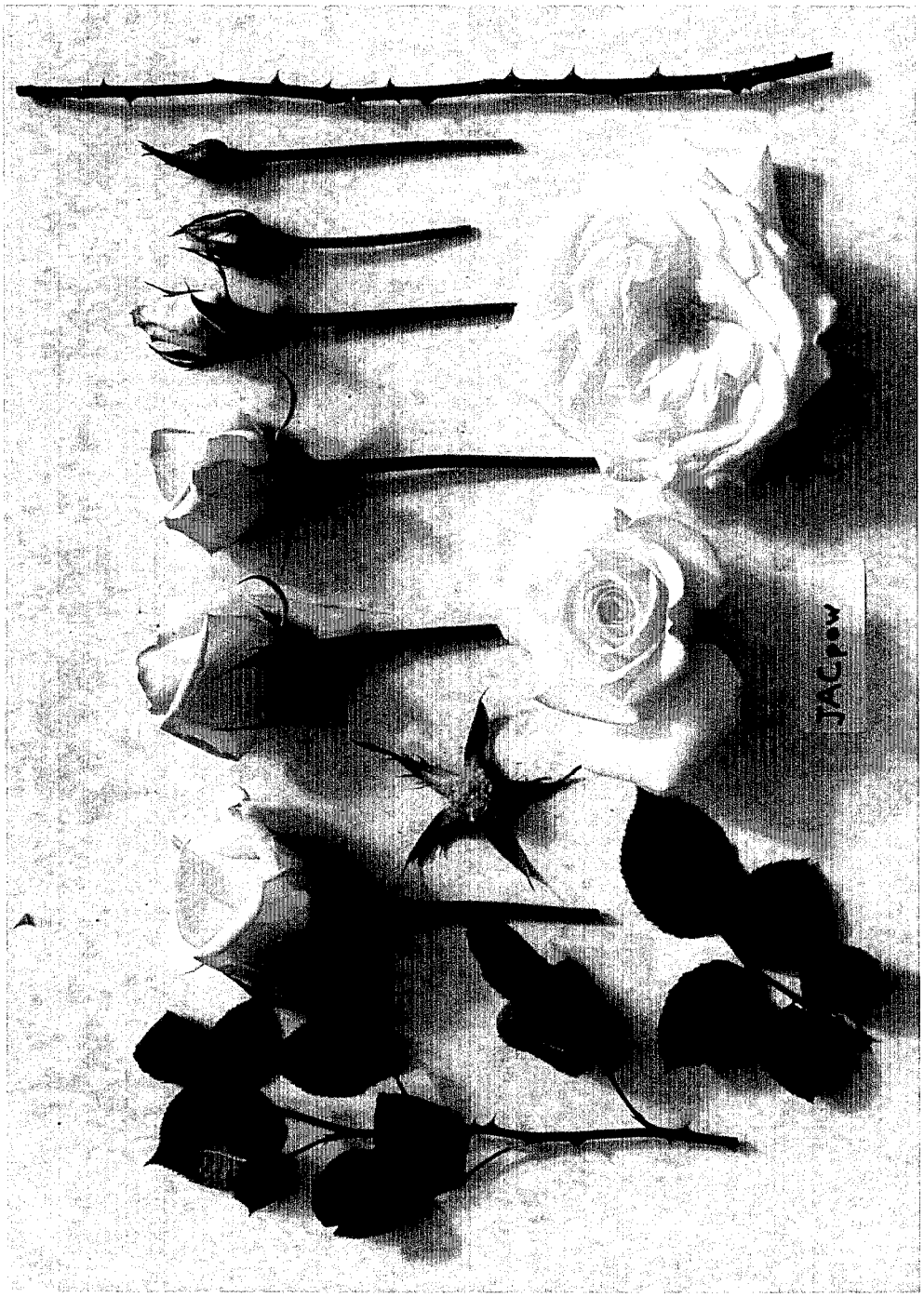
JACpow